(12) United States Patent
Potts et al.

(10) Patent No.: US 8,852,255 B2
(45) Date of Patent: Oct. 7, 2014

(54) MICROPROCESSOR CONTROLLED MEDICAL LASER DEVICE

(76) Inventors: Richard Allen Potts, Ferndale, WA (US); Larry Ray Potts, Portland, OR (US)

(*) Notice: Subject to any disclaimer, the term of this patent is extended or adjusted under 35 U.S.C. 154(b) by 549 days.

(21) Appl. No.: 13/112,667

(22) Filed: May 20, 2011

(65) Prior Publication Data
US 2012/0296401 A1 Nov. 22, 2012

(51) Int. Cl.
*A61N 5/067* (2006.01)
*A61B 19/00* (2006.01)

(52) U.S. Cl.
CPC ......... *A61B 19/201* (2013.01); *A61B 2019/202* (2013.01)
USPC .................................. 607/90; 607/88; 607/89

(58) Field of Classification Search
USPC ............. 607/88–91; 606/1, 2, 10, 13; 33/227, 33/276, 282, 286, 290–292; 356/21, 138, 356/139, 139.03–139.09, 140, 141.1–141.5
See application file for complete search history.

(56) References Cited

U.S. PATENT DOCUMENTS

| 7,354,431 | B2 * | 4/2008 | Wilson | 604/540 |
| 7,591,074 | B1 * | 9/2009 | Potts et al. | 33/290 |
| 2012/0224171 | A1 * | 9/2012 | Yotz et al. | 356/121 |

OTHER PUBLICATIONS

E. Bermmark, C. Wiktorin, "A triaxial eccelerometer for measuring arm movement," Applied Egronomics, 33 (2002), pp. 541-547.*

* cited by examiner

*Primary Examiner* — Ahmed Farah
(74) *Attorney, Agent, or Firm* — Mark S. Hubert

(57) ABSTRACT

A microprocessor controlled medical laser device that has a precise laser beam alignment system indicated by a series of sequentially color changing LEDS. The power management system adjusts the LED'S power input so as maximize battery life, increasing it by up to six times. It's alignment is enabled by a triaxial accelerometer that may be accurately calibrated horizontally or to a plethora of angles relative to the horizontal axis. It is shock resistant and times out to turn the laser off after a predetermined time.

11 Claims, 5 Drawing Sheets

MICROPROCESSOR CONTROLLED MEDICAL LASER DEVICE

BACKGROUND OF THE INVENTION

The present invention relates to a laser device that will enable the precise vertical positioning of a plethora of medical sensors, drainage systems, intubation systems, intravenous devices, catheters and the like with respect to a specific point on the patient's anatomy. This specific point may be the heart, the brain, a PIC line insertion point, or a drainage line insertion point.

Precise measurement of a patients vital statistics is critical with very small changes in pressure due to elevation, often having dramatic effects of drainage or supply rates, monitored pressures, static pressure scales, etc. The accurate positioning of the related sensors, scales, fluid lines and the such with respect to elevation the patient's body has heretofore been done with laser beams coupled to crude leveling devices. The battery life of these devices is generally short as the laser light's power output far exceeds what is actually needed for short range leveling. Further these early devices are susceptible to loss of accuracy by the initial calibration process, the eye of the user, the illumination of the room and from sharp impacts. Additionally, the connection of these devices to the vast array of different medical suppliers equipment and supports is problematic. Lastly, many of the prior art leveling systems are not designed to be used on either side of the patient and cannot be recalibrated.

None of the existing prior art systems allow for angular use such as would be helpful for the specific angular alignment of patient's anatomy while they go through an X-ray machine, and MRI scanner or a CAT scanner.

Henceforth, a medical laser device that could overcome the described downfalls of the prior art would fulfill a long felt need in the medical industry. This new invention utilizes and combines known and new technologies in a unique and novel configuration to overcome the aforementioned problems and accomplish this.

SUMMARY OF THE INVENTION

The general purpose of the present invention, which will be described subsequently in greater detail, is to provide a laser device for the accurate and precise alignment of medical devices to a specific point on the patient's body.

It has many of the advantages mentioned heretofore and many novel features that result in a new medical laser alignment system which is not anticipated, rendered obvious, suggested, or even implied by any of the prior art, either alone or in any combination thereof.

In accordance with the invention, an object of the present invention is to provide an improved medical laser alignment system capable of detachment and reuse on disposable medical drain/drip systems.

It is another object of this invention to provide an improved medical laser alignment system capable of bidirectional horizontal indication by rotation of the laser about a pivot point.

It is an object of this invention to provide a medical laser alignment system that uses a multiple zero reference for the setting of the triaxial accelerometer's reference accuracy.

It is a further object of this invention to provide a medical laser alignment system that orientates its horizontal axis of illumination to the zero reference point of a triaxial accelerometer.

It is still a further object of this invention to provide for a rotatable medical laser alignment system that allows leveling for a horizontal laser light beam projection by a set of easy to see indicator lights rather than by a crude bubble level.

It is yet a further object of this invention to provide a compact, reliable medical laser alignment system that has programable accuracy, power saving features, a low battery alarm and which can be programmed such that the zero reference point of its triaxial accelerometer may be set to calibrate the laser light beam for a plethora of angles with respect to the horizontal.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements. Other objects, features and aspects of the present invention are discussed in greater detail below.

DETAILED DESCRIPTION

Figure 1:
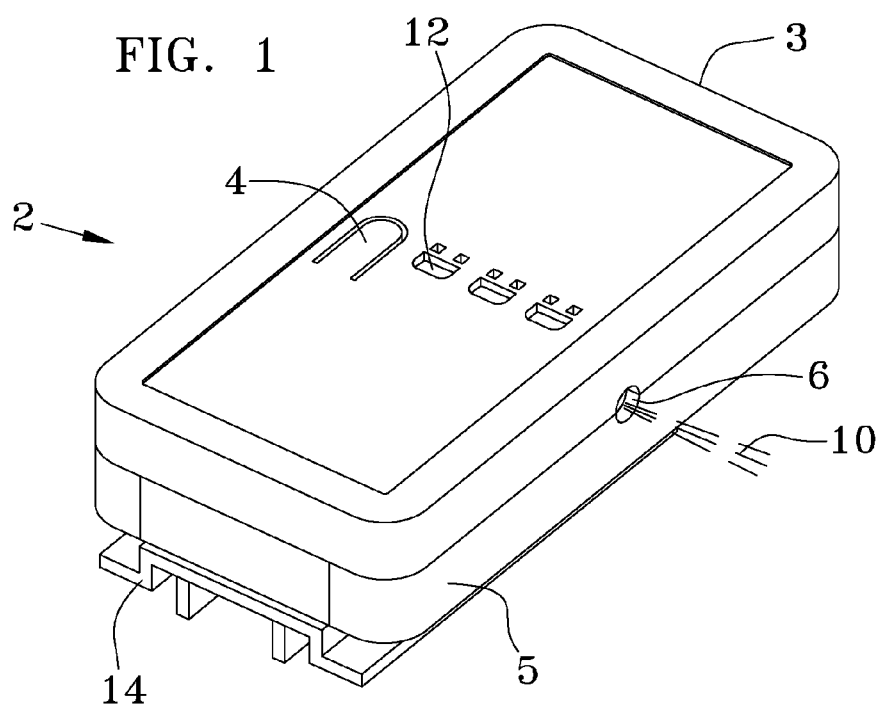
FIG. 1 is a front perspective view of the medical laser device.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

When discussing three dimensional coordinates herein, Cartesian coordinates are used. Thus for any particular point, there is an x, y, and z coordinate, which typically correspond to how far the object is left and right, forward and back, and up and down respectively.

The medical laser device described herein enables the precise positioning of a plethora of medical sensors, drainage systems, intubation systems, intravenous devices, catheters and the like with respect to a specific point on the patient's anatomy. For example, in many medical procedures a catheter connected to either a drainage bag or a drip bag is inserted into an opening in the human body for pressure monitoring, or the addition or removal of fluids. This is commonly done in the patient's intracranial, intravascular, intracardiac, intrapulmonary or intrafascial compartments. The pressure at the point of the opening is often critical, as the differential pressure between this and the fluid level in the bag is the motive force for the movement of the fluids. For this fluid movement to be accomplished at a controlled rate, the differential pressure between the insertion point and the bag's fluid level must be accurately known. This requires that a precise vertical alignment of the "zero point" on the static pressure scale of the bag be made. This is accomplished through the vertical alignment of a horizontal laser beam with the insertion point of the catheter. In another medical procedure it is typical to have the patient's head angled at approximately 30° with respect to the horizontal axis when the patient passes through a horizontal CAT scanner. This is accomplished by alignment of the patient's head with an angular laser beam calibrated to 30° and positioned on the bedway of the CAT scanner.

Figure 2:
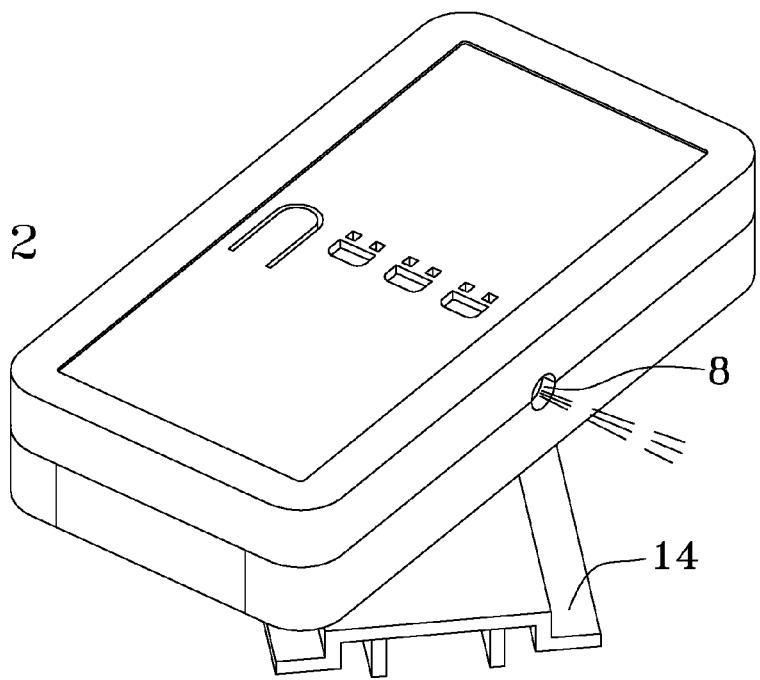
FIG. 2 is a front perspective view of the medical laser device with a first bracket rotated.

Looking at FIGS. 1 and 2 the front face and operational side of the case top 3 of the microprocessor controlled medical laser device 2 can best be seen. The case is a two part assembly made of a case top 3 and a case bottom 5. The "ON" tab 4 is simply a U shaped cutout on the front face of the case top 3 of the laser device 2 that is able to elastically deform and flex inwards to contact the "ON" switch on the internal printed circuit board (PCB) that activates the laser diode. There is no "OFF" control of this switch as this is accomplished by a timed operation (generally set for the 30 to 40 second range) of the microprocessor. The laser diode 8 resides on the side of the PCB in alignment with the laser orifice 6 so as to allow the laser light beam 10 to project from the side of the case 3. The top ends of three light tubes 12 extend into three orifices cut into the case top 3. The bottom ends of these light tubes reside adjacent to three multicolor LEDs on the PCB. A first mounting bracket 14 is pivotally affixed to the case back 5.

In operation, the user need only affix the proper mounting bracket to the case back 5, attach the mounting bracket onto the piece of associated equipment or support pole, depress the "ON" tab 4, point the laser light beam 10 to the desired spot on the patient while tilting the device 2 in the z axis until all three of the LEDS have sequentially changed from red to solid green, and then affixing the laser device 2 and associated equipment at this elevation.

Figure 3:
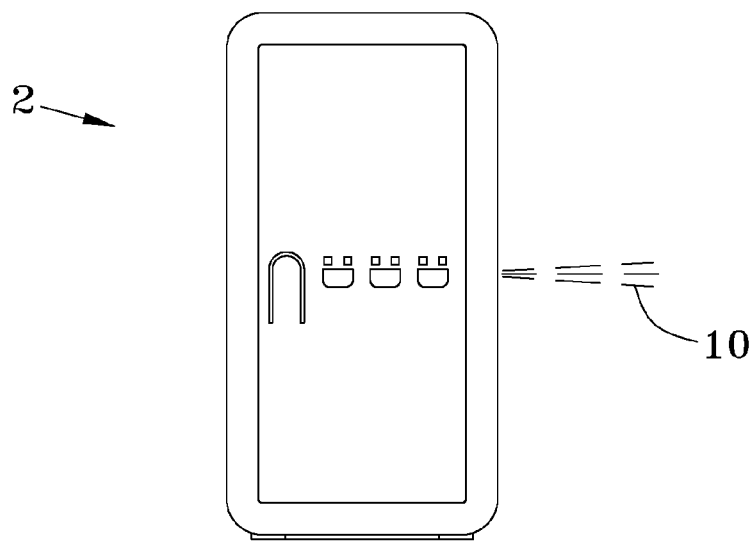
FIG. 3 is a front view of the medical laser device.
Figure 4:
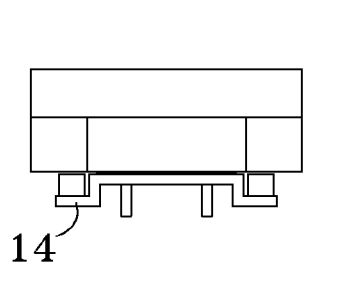
FIG. 4 is an end view of the medical laser device with the first bracket installed.
Figure 5:
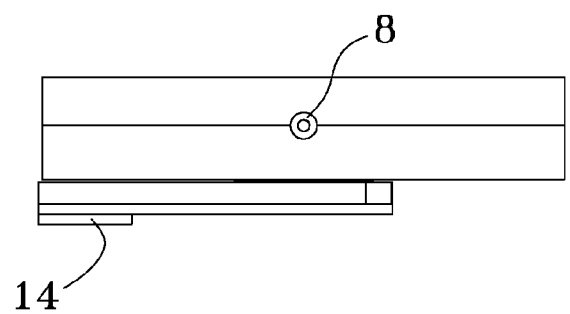
FIG. 5 is a side view of the medical laser device with the first bracket installed.

Looking at FIGS. 3, 4 and 5 it can be seen that the laser device 2 is generally rectangular with a thin profile where the laser light beam 10 projects centrally from one side. The bracket 14 is shorter than the device 2 and attaches centrally to the laser device 2.

The body of the laser device 2 generally resides such that during normal operation, its longitudinal axis lies in the YZ or XZ (vertical) planes (its longitudinal axis is parallel to the Z axis) so that its laser light beam 10 projects normally (parallel to the XY plane) therefrom in the XY (horizontal) plane. It is free to rotate about the X or Y axis in this configuration.

Figure 6:
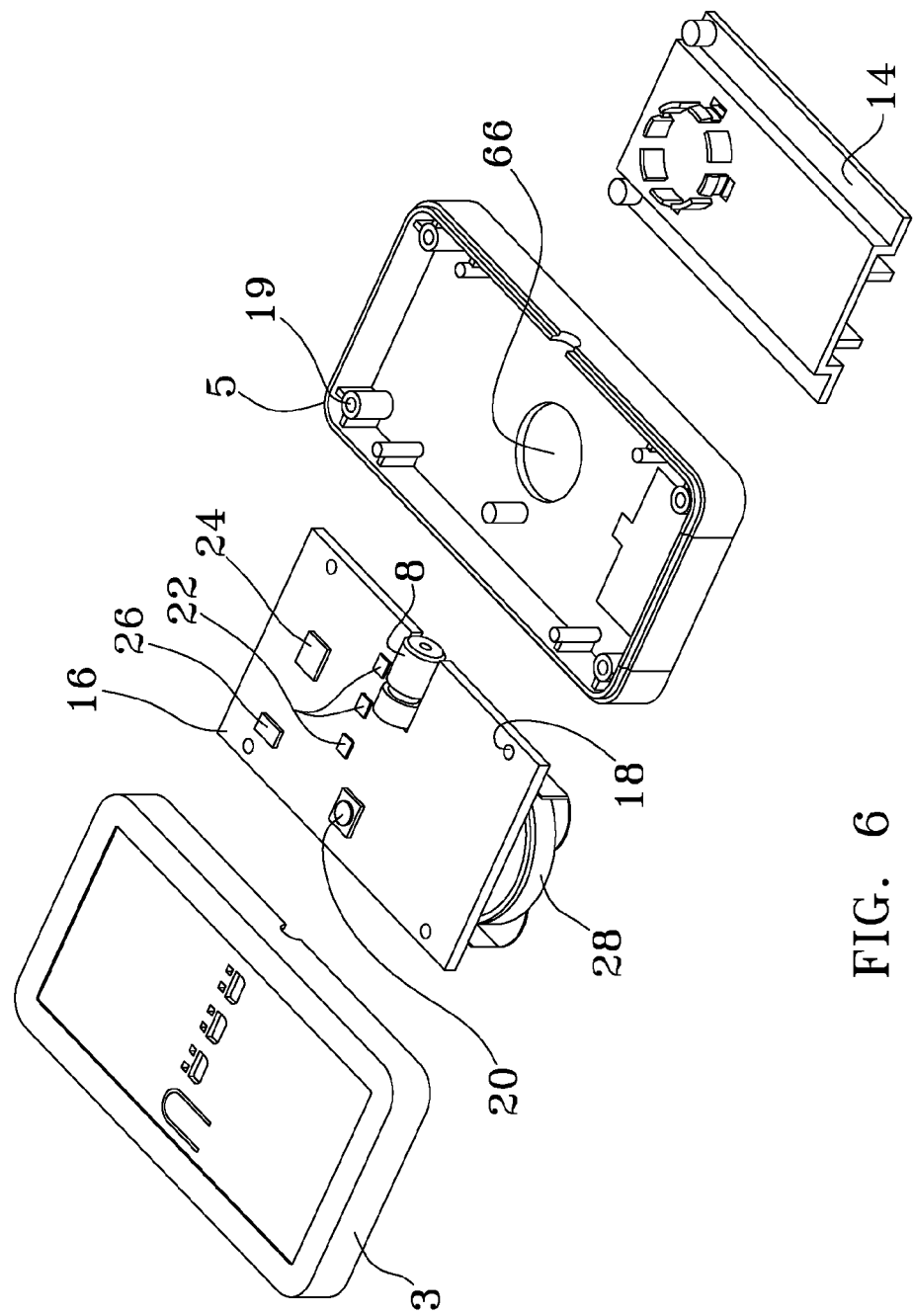
FIG. 6 is a front perspective assembly view of the medical laser device showing the location of all the key elements.
Figure 7:
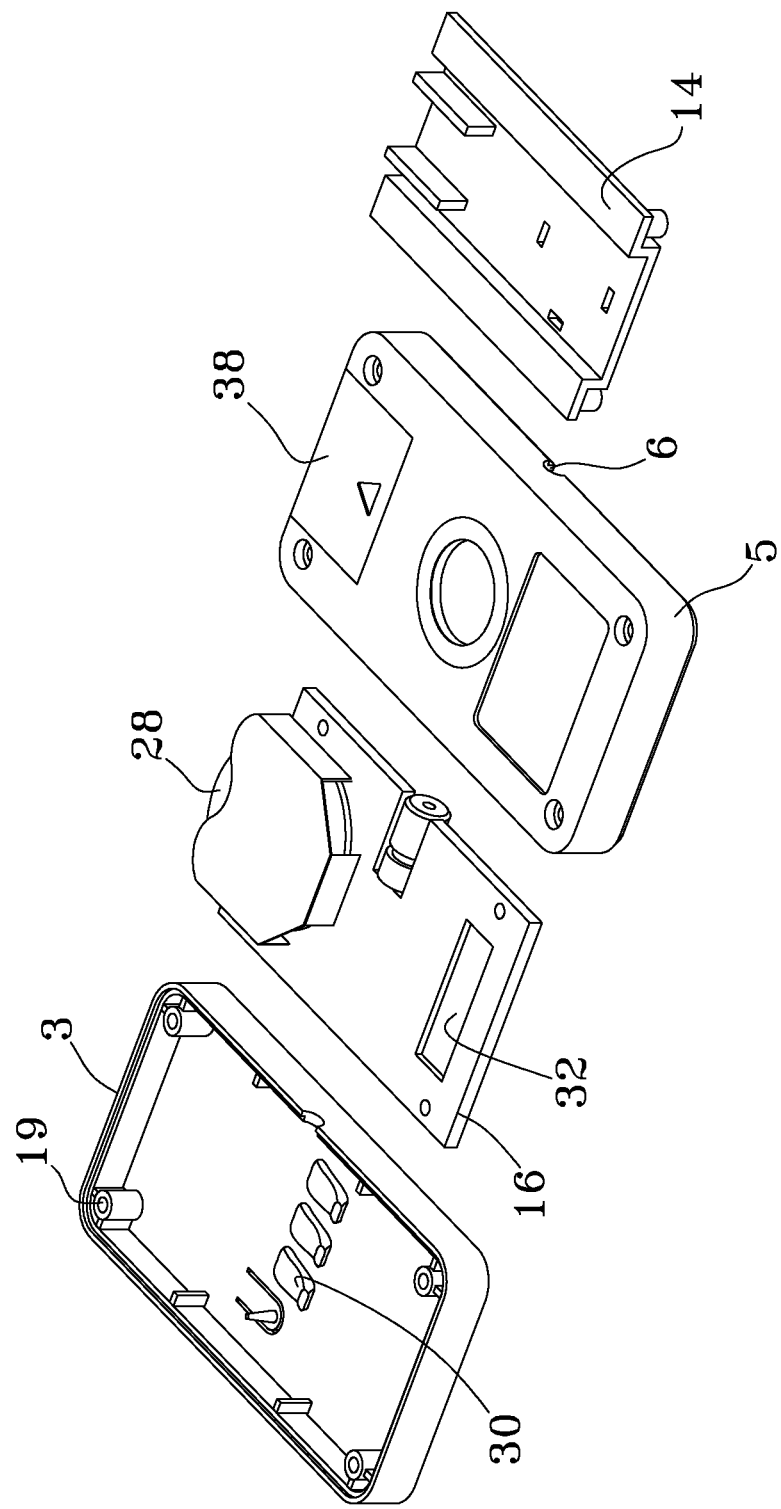
FIG. 7 is a rear perspective assembly view of the medical laser device showing the location of all the key elements.
Figure 8:
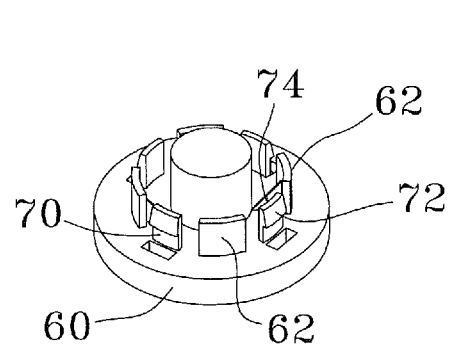
FIG. 8 is a perspective view of the generic rotatable quick change attachment mechanism as formed on the front of the second alternate embodiment bracket.
Figure 9:
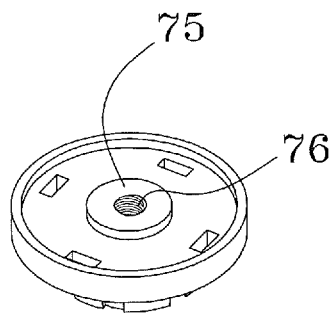
FIG. 9 is a perspective view of the back of the second alternate embodiment bracket.

FIGS. 6 and 7 show disassembled laser devices 2. The components are organized left to right in their order of disassembly from the case top 3 to the case bottom 5 (FIG. 6) and in their order of disassembly from the case bottom 5 to the case top 3 (FIG. 7). The PCB 16 houses all of the functional components and is held in a spaced configuration within the case top 3 and case bottom 5 by a set of screws threadingly affixed in the aligned corner sockets 18 of the case's halves, passing through positioning orifices 19 in the corners of the PCB 16. When assembled, the PCB aligns within the case such that the laser diode 8 resides adjacent the laser orifice 6, the "ON" switch resided directly beneath the "ON" tab 4 and the light tubes 30 have their bottom ends directly over the top surface of the LEDS 22 and their top ends 12 extending through three orifices cut into the case top 3. These three externally polished light tubes direct the LEDS' light to the surface of the laser device 2 through a torturous bending path. These light tubes 30 are rigidly affixed to the inside surface of the case top 3.

The PCB 16 houses in electrical connectivity the following: an "ON" switch 20; (30 sec delay automatic off) a trio of dual color (red/green) led level indicating lights 22 (red green); a triaxial accelerometer 26; a microprocessor 24; a laser diode 8; a power supply 28 (3 volt Cr 2450 Lithium coin battery) accessible through door 38; and a connection socket 32.

A triaxial accelerometer was selected for its three orthogonal internal sensing elements to enable simultaneous multi-axis measurements in the x, y, and z-axes.

The microprocessor 24 has a flash memory, a real time clock, a timer, a power output adjustment (the laser diode is rated to operate at a maximum of a 1 milliwatt but the microprocessor limits the power input to the laser diode at 0.5-0.9 milliwatt to reduce power consumption since the laser beam generally only extends a max of 10 feet) a multiple zero reference, (for laser accuracy) a voltage reference turn off, (for battery low power operation) and a low power visual alert (when battery voltage drops below a preset lower limit the accuracy of the accelerometer begins to decline so the microprocessor makes all three red LEDS blink signaling the need for a battery change.) A connector socket 32 allows for signal connectivity between the microprocessor 24 and the programming and calibration equipment as well as for the connection of a monitor for the visual display of the microprocessor outputs. Using this connector socket 32 a two digit lcd screen may be attached that will provide a visual user interface to indicate the angle of the laser light beam with respect to the horizontal XY plane. The triaxial accelerometer 26 is rigidly mounted to the PCB 16 as is the laser diode 8 such that hard knocks will not disturb the accuracy of the laser device 2. Recalibration is not necessary after the initial set up has been accomplished.

In the assembly of the laser device's PCB 16 the laser diode 8 is generally aligned to emit the laser light beam 10 perpendicular to the longitudinal axis of the PCB 16 (which has its longitudinal axis in line with the longitudinal axis of the device's case. (This is done by physical alignment with precise mechanical jigs.) To accomplish this the PCB 16 is put into a jig that holds its longitudinal axis parallel to the Z axis. The jig has a set of spring loaded programming connections (terminals) that matingly contact the programming terminals of the connector socket 32 for the microprocessor 24 on the PCB 16. The laser diode 8 is energized so as to shoot the laser light beam 10 approximately horizontal (in the XY plane) and project it onto a first reference point some distance away. (approximately 1 meter) If the laser light beam 10 does not shine on this reference point then the laser diode is mechanically adjusted (by altering the hard soldered power connectors that affix the laser diode 8 to the PCB 16) until it does. Then the programming unit applies the correct algorithms to determine a first zero point reading. The laser device 2 is then rotated 180 degrees such that its longitudinal axis still resides parallel to the Z axis. This procedure is repeated with respect to a second reference point at the same vertical elevation. The programing unit applies algorithms that uses these first and second readings to establish a true zero point reading for the triaxial accelerometer's reference grid and inputs this value to the microprocessor. (Thus when the triaxial accelerometer 26 sends a signal to the microprocessor 24 that the laser device 2 is positioned at this zero point, the laser light beam 10 is projecting horizontally or it is "level".) Since the triaxial accelerometer 26 and the laser diode 8 are both mechanically fixed on the PCB 16 this calibration is good for the life of the laser device 2. The microprocessor 24 selectively changes the color of the LEDS 22 from red to green as the signal from the triaxial accelerometer 26 indicates that it is approaching the zero point. The LEDS 22 are arranged in a row of three. The LED 22 nearest the laser diode 8 goes from red to green when the longitudinal axis of the laser device 2 is within ½th of a degree plus or minus of the zero point. The middle LED goes from red to green when the longitudinal axis of the laser device 2 is within ¼ of a degree plus or minus of the zero point. The light furthest the laser diode 8 goes from red to green when the longitudinal axis of the laser device 2 is within ⅛th of a degree plus or minus of the zero point. Accordingly, when all three LEDS 22 have changed from red to green and remain solid green the laser light beam 10 will also be projecting at ⅛th of a degree plus or minus of the horizontal axis. In an alternate, lower costing embodiment, one of the end three lights will always be green if the beam is not level, and the remaining two lights will both turn from red to green when the device 2 is less than ½ of a degree horizontal. It should be noted that other timing/indication configurations are well know in the art and could be utilized without departing from the scope of this invention.

Simply stated, the triaxial accelerometer generates and sends an electronic signal to the microprocessor 24 that represents the axial position of the laser device 2 relative to the horizontal X or Y axis. Then the microprocessor 24 applies an algorithm based on this position and generates and sends an electronic instruction that determines what color each LED 22 emits.

It is to be noted that the laser device 2 in a similar fashion to that explained above, may be calibrated so as to adjust the zero reference scale of the triaxial accelerometer 26 to any desired horizontal angle so that the laser unit may be used to align any device to a set angle without the use of a visual display connected to the device 2 through the connection socket 32 as discussed above. This is a handy feature that finds a plethora of applications outside of the medical industry.

Looking at FIGS. 6, 8, 9 and 10 the design and configuration of the attachment mechanism can best be seen on two different mounting brackets and its operation explained. The attachment mechanism may be fabricated onto any style of removable bracket to accommodate different medical device's mounting plates. For example, the round bracket 60 has a reinforced central section 75 that accommodates a threaded insert 76 that allows the bolted attachment of any bracket or device. The first mounting bracket 14 has a specific configuration for sliding engagement with a certain manufacturer's device. The attachment mechanism allows each bracket to be self tightening and additionally, interchangability of brackets is of a quick change, self adjusting style. Looking at FIG. 8, the attachment mechanism has a total of 8 projections arranged in a circular fashion that extend normally from the face of the round bracket 60. There are 4 preloaded tabs 62 and 4 snap hooks 64 that are equally interspersed. Where there is a need to hold the laser device 2 in very tight locations there is a recess on the back side of the bracket that holds a double sided adhesive patch.

Figure 10:
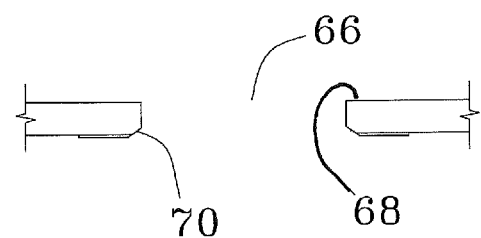
FIG. 10 is a cross sectional view of the mounting orifice in the case bottom.

Looking at FIG. 10 it can be seen that the circular mounting orifice 66 has an outer beveled peripherial ring 70 residing centrally about the orifice 66. When the bracket 60 is being pressed into the orifice 66, the beveled ring 70 acts to guide the snap hooks 64 such that they flex slightly inward (elastically deform) as they pass through the orifice 66 and then flex back to their original position such that the angled lock tooth 72 on each of the four snap hooks 70 engages behind the orifice 68 once the lock tooth 72 passes beyond the trailing edge 68, thereby constraining the bracket 60 to the laser device's bottom case 5. The four preload tabs 62 bear against the central raised flange 70 to provide frictional resistance for the rotation of the bracket 60 in the orifice 66 and to stabilize the bracket 60 with respect to the bottom case 5. Each of the preload tabs 62 have stiffening or strengthening supports 74 to allow for repeated flexing without breaking or loss of tensioning ability. Only one of the snap hooks 64 has such a strengthening support 74. (FIG. 8) Testing has shown that one of the tabs historically has failed and requires the tab. Engagement of any bracket bearing the attachment mechanism to the bottom case 5 is accomplished by simply pressing, centrally, the two parts together. Removal is accomplished by pulling the bracket off from a single, off centered point on the bracket. Once engaged the bracket can be freely rotated with respect to the laser device 2 yet there is enough friction exerted between the 8 projections of the attachment mechanism and the orifice 66 to hold the device 2 in any orientation.

The obvious advantages of the microprocessor controlled medical laser device is that it is fast and easy to use with a high level of accuracy and reliability that is shock resistant and can be used by people with poor vision. It is capable of calibration for any desired angle, quick attachment to a plethora of mounting brackets, and has an extended battery life that lasts up to 6 times longer because of the lowered LED power output as managed by the microprocessor.

The above description will enable any person skilled in the art to make and use this invention. It also sets forth the best modes for carrying out this invention. There are numerous variations and modifications thereof that will also remain readily apparent to others skilled in the art, now that the general principles of the present invention have been disclosed. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Having thus described the invention, what is claimed as new and desired to be secured by Letters Patent is as follows:

1. A microprocessor controlled medical laser device comprising:
   a case comprised of a front half casing and a back half casing;
   a printed circuit board that serves to rigidly house and keep in electrical connectivity a triaxial accelerometer, a microprocessor, a DC power source, a laser diode, a number of dual colored LEDs, a connection port and a power switch;
   wherein said printed circuit board is rigidly mounted in a centrally spaced configuration inside said case.

2. The microprocessor controlled medical laser device of claim 1 wherein the number of LEDS is three.

3. The microprocessor controlled medical laser device of claim 2 wherein said triaxial accelerometer generates and sends an electronic signal to said microprocessor that is translated into the relative axial horizontal position of the device, and said microprocessor applies an algorithm based on said position to generate and send electronic instructions to each LED that effects what color the LED emits.

4. The microprocessor controlled medical laser device of claim 1 further comprising three light tubes affixed to said front half casing and positioned so as to each have a first end adjacent to at least one of said LEDs and a second end extending into a LED orifice formed through the front half casing so as to project a light of the LED outside of said casing.

5. The microprocessor controlled medical laser device of claim 1 further comprising:
a bracket removably affixed about the periphery of an orifice formed centrally through said back half casing.

6. The microprocessor controlled medical laser device of claim 5 wherein said bracket has an attachment device thereon adapted for mechanical engagement about said periphery of said orifice, made of a circular arrangement containing snap hooks with angled locking teeth that flex slightly inward when passed through said orifice and then flex back to their original position such that the angled lock tooth on each of the snap hooks engages behind the orifice.

7. The microprocessor controlled medical laser device of claim 5 further compromising a circular arrangement, which also contains preload tabs with stiffening supports, said preload tabs adapted to provide frictional resistance in said orifice for the rotation of the bracket.

8. The microprocessor controlled medical laser device of claim 1 wherein said laser diode on said printed circuit board resides adjacent an opening in said case so as to allow a laser light beam generated by said laser diode to extend there through.

9. The microprocessor controlled medical laser device of claim 8 wherein said power switch on said printed circuit board resides directly below a U shaped cutout in said front half casing.

10. The microprocessor controlled medical laser device of claim 9 wherein said microprocessor has a power management system that regulates the power that is sent to regulate the intensity of the laser light beam generated by said laser diode.

11. The microprocessor controlled medical laser device of claim 9 wherein said microprocessor's said power management system monitors remaining power of said DC power source and generates a visual alert of flashing LEDS when said remaining power drops below a preset level.

* * * * *